B. SHERWOOD.

Trusses.

No. 5,854. Reissued April 28, 1874.

Witnesses.
Philip F. Garner
A. B. Cauldwell

Inventor.
Benjamin Sherwood
By M. M. Wood
Attorney

AM. PHOTO-LITHOGRAPHIC Co. N. Y. (OSBORNE'S PROCESS.)

UNITED STATES PATENT OFFICE.

BENJAMIN SHERWOOD, OF BROOKLYN, ASSIGNOR TO GEORGE W. GREGORY, OF SYRACUSE, NEW YORK.

IMPROVEMENT IN TRUSSES.

Specification forming part of Letters Patent No. 44,226, dated September 13, 1864; reissue No. 5,854, dated April 28, 1874; application filed April 16, 1874.

*To all whom it may concern:*

Be it known that I, BENJAMIN SHERWOOD, formerly of the State, county, and city of New York, now of Brooklyn, New York, am the inventor of certain Improvements in Trusses, of which the following is a specification:

It is well known that hernia or rupture is generally caused by the effort of the bowels to expand under strain, as in lifting, or by violent bodily exertion. The straining incident to such exertion causes great pressure on the bowels, inducing an outward movement of the abdomen, and a strong downward pressure on the walls of the belly. When hernia exists, this strain tends to a protrusion of the bowels at the rupture.

The aim of this invention is to produce a truss which will act by impact against the abdomen, and said truss so constructed that the outward movement of the upper portion of the abdomen, caused by any strain thereof, will, in pressing the upper portion of the plate out, throw the lower portion with corresponding pressure against the lower portion of the abdomen, thereby preventing protrusion of the bowels at the rupture, or the formation of new rupture.

This invention consists of a plate having its surface provided with numerous openings or perforations, and shaped to fit the lower portion of the abdomen, said plate being provided at its back with teats or equivalents, which may be easily engaged with a clasp or buckle which acts as a swiveling connecting device between a body-belt and the plate. The clasp is capable of free movement without moving the plate or disturbing the pressure. The body-band is pliable. This truss or instrument is also well adapted to the purposes of an abdominal supporter.

Figure 1:
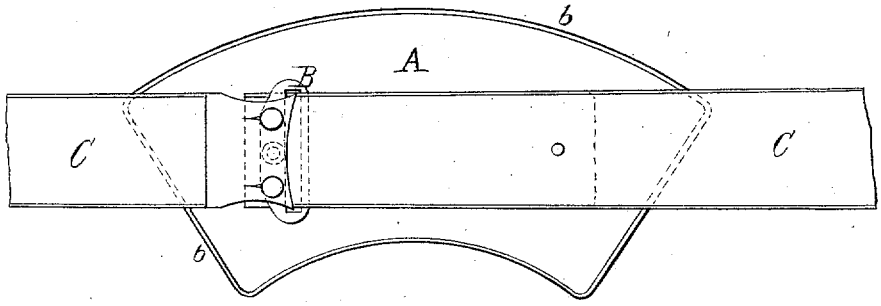
Figure 2:
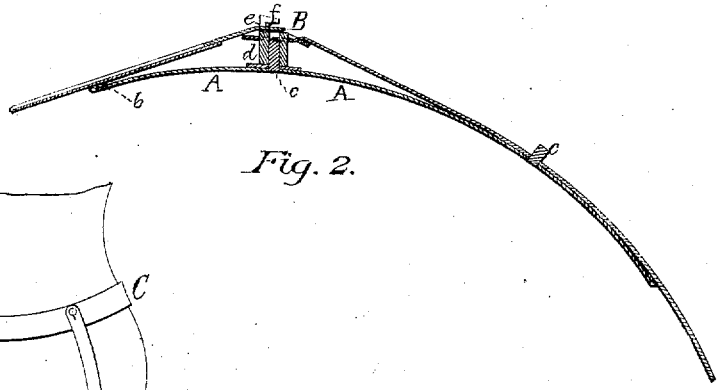
Figure 3:
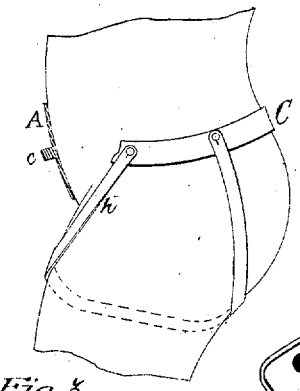
Figure 4:
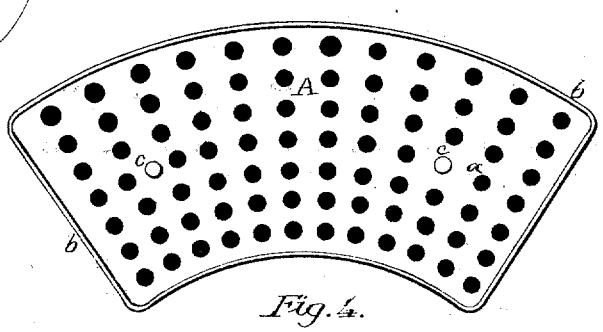
Figure 5:
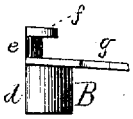
Figure 6:
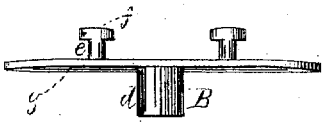

In the drawing, Figure 1 is a front view of the plate with belts attached, the perforations not being shown; Fig. 2, a longitudinal section with belt and clasp; Fig. 3, a section of the plate shown as applied to the abdomen; Fig. 4, a back view of the perforated plate, showing the teats thereon; Figs. 5 and 6, side and end views of the clasp or buckle.

The plate A is made of sheet metal, but may be made of any material that will retain its shape, and is provided throughout its whole surface with numerous small openings, *a*. The edges *b* of this plate are flanged or bent over toward the back of the plate, and at the back are teats *c*, or equivalents, which project outwardly. A teat is engaged by a clasp or buckle, B, which serves as a readily detachable and attachable fastening for connecting the plate with the pliable body-belt C. These teats are located in the same horizontal line, but are nearer the lower than the upper edge of the truss-plate, so as to give the abdomen greater leverage on the upper portion of the plate, the clasp acting as the fulcrum. The plate when so rocked presses its lower portion closely against the abdomen. The plate will occupy the larger surface of the lower portion of the abdomen between the groins, and the two lower corners of said plate cover the place where rupture usually occurs or exists. The body belt or band C is made of a material nearly or quite inelastic and pliable. The clasp or buckle B has a projection or socket, *d*, on its under side to engage the teat, or equivalent, on the back of the plate. The clasp or buckle can turn freely or swivel on the teat without moving the plate, and this is a very important feature of this invention. This plate when placed in position on the abdomen should have no tendency to be moved or shifted with relation to the portion of the abdomen with which it is in contact, yet it ought to be free to move out and in with the abdomen, and to adapt itself to the outward movement of the abdomen when strain occurs, as described. The teat and clasp thus constitute swivel-like connection, allowing the plate to remain, as it were, seated and immovable, with reference to the surface of the abdomen, notwithstanding its out and in movements, and the movements of the body-strap in walking, &c. The buttons *e* have flanged heads *f*, larger than their shanks, and they are turned toward the opening *g* in the clasp, through which the belt-strap is passed. One end of the belt-strap is secured through this opening, and the other end engages with the buttons or flanged heads *f*.

In all truss-plates prior to this invention, the thigh-strap or ligature *h* has been secured at one of its ends directly to the truss-plate, which is objectionable, inasmuch as it does not permit the truss to keep its position on the abdomen, for movement of the body and belt straps is liable to change the position of the plate on the abdomen. The ligature *h* in this invention is not attached to the truss-plate, but is attached to the body-belt at the back, and also at the front, at a suitable distance from the pivotal point.

The truss shown in the drawings is intended for a rupture on one side only, and, therefore, there is but one teat shown as used for a fulcrum. Sometimes, however, two fulcrums are used, one on each side, and this depends on the nature of the case. Pads of any well-known form may be attached to the truss, if deemed requisite.

I do not confine myself specifically to all the details of construction as set forth, so long as the principle of action of the instrument is the same.

I am aware that a plain metallic truss-plate, having slots at each lower corner for adjustment of pads, and provided with pads, and connected by screws at top corners of plate with steel springs to grasp the body, has been employed; but such a device I do not claim, as it does not possess the advantages possessed by this invention; and I am also aware that truss-pads have been made of wood, of ivory, of padded blocks, of india-rubber, and of metal and ivory perforated with numerous small holes for ventilation. I am unaware, however, that this has ever been applied, prior to my invention, to abdominal truss-plates.

Having described my invention, I claim—

1. The metallic perforated abdominal truss-plate with flanged edges, substantially as described.

2. A metallic perforated abdominal truss-plate with flanges bent or turned backward, and provided with teats, or equivalents, in combination with the pliable body-belt and the metallic clasp.

3. A perforated abdominal truss-plate, shaped to conform to and extend nearly across the abdomen, and provided with teats or equivalents projecting from the back, by which the truss is adapted to be easily connected and disconnected from the pliable body-belt.

4. The combination of the perforated abdominal truss-plate, having teats or equivalents, with the slotted clasp or buckle, provided with buttons, the shanks of which are smaller than the heads, and the heads of which are turned toward the slot.

5. A perforated abdominal truss-plate with teats or equivalents, located at each side of a line drawn vertically through the center of the plate, and nearer the bottom than the top of the plate, in order that when the plate is pressed against the abdomen by the body-belt, and strain is exerted on the abdomen, that outward movement of the abdomen acting on the top of the plate will press its lower portion against the lower portion of the abdomen with greater force.

6. In combination, the abdominal truss-plate, a loosely-connected or swiveling clasp or buckle, a pliable body-strap, and a ligature or thigh-strap, disconnected from the truss-plate but attached to the body-belt.

7. The clasp or buckle, provided with a slot for one end of the body-strap, and adapted to swivel on and connect with the teat or equivalent at the back of the truss-plate.

BENJAMIN SHERWOOD.

Witnesses:
H. M. BAKER,
M. A. BAKER.